United States Patent [19]

Iwata et al.

[11] Patent Number: 5,217,970

[45] Date of Patent: Jun. 8, 1993

[54] USE OF ISOXAZOLIN-3-ONE DERIVATIVES AS ANTIDEPRESSANTS

[75] Inventors: Nobuyoshi Iwata; Kenji Yoshimi; Mitsuo Nagano, all of Tokyo, Japan

[73] Assignee: Sankyo Company, Limited, Tokyo, Japan

[21] Appl. No.: 856,494

[22] Filed: Mar. 24, 1992

Related U.S. Application Data

[62] Division of Ser. No. 537,517, Jun. 13, 1990, Pat. No. 5,116,839.

[30] Foreign Application Priority Data

Jun. 26, 1989 [JP] Japan .................. 1-162940
Aug. 22, 1989 [JP] Japan .................. 1-215607
Oct. 11, 1989 [JP] Japan .................. 1-264706

[51] Int. Cl.$^5$ ............... A61K 31/535; A61K 31/40; A61K 31/42; A61K 31/54
[52] U.S. Cl. ............... 514/231.2; 514/236.8; 514/225.5; 514/226.5; 514/231.5; 514/254; 514/233.8; 514/235.5; 514/237.5; 514/378; 514/380; 514/408; 514/414
[58] Field of Search ............... 514/414, 416, 378, 379, 514/380, 236.8, 237.5, 235.5

[56] References Cited

U.S. PATENT DOCUMENTS

| | | | |
|---|---|---|---|
| 4,505,921 | 3/1985 | Beregi et al. | 514/212 |
| 4,579,860 | 4/1986 | Tomita et al. | 514/380 |
| 4,849,441 | 7/1989 | Okazaki et al. | 514/414 |
| 4,863,948 | 9/1989 | Arrowsmith et al. | 514/416 |

FOREIGN PATENT DOCUMENTS

| | | |
|---|---|---|
| 0273744 | 7/1988 | European Pat. Off. |
| 0334674 | 9/1989 | European Pat. Off. |
| 0335723 | 10/1989 | European Pat. Off. |
| 67275 | 9/1973 | Japan . |
| 157925 | 12/1978 | Japan . |
| 86766 | 6/1980 | Japan . |

OTHER PUBLICATIONS

Patent Abstracts of Japan, vol. 12, No. 467 (C-550) [3314], Dec. 7, 1988 of JP-A-63-188625 (Mitsui Toatsu Chem. Inc.) Apr. 8, 1988, Japan.
Patent Abstracts of Japan, vol. 5, No. 89 (C-58) [761], Jun. 1981 of JP-A-5634674 (Sankyo K.K.), 6-4-1081; Japan.
Patent Abstracts of Japan, vol. 6, No. 90 (C-104)[1968], May 27, 1982 of JP-1-5721377 (Shinogi Seiyaku K.K.) Apr. 2, 1982; Japan.

*Primary Examiner*—Frederick E. Waddell
*Assistant Examiner*—T. J. Criares
*Attorney, Agent, or Firm*—Frishauf, Holtz, Goodman & Woodward

[57] ABSTRACT

A method of treating depression comprising administering to a patient an effective antidepressive amount of a compound of the formula $$\begin{array}{c} R^2 \\ R^1\diagdown \overset{|}{C} \\ \phantom{R^1\diagdown}C{=\!=\!=\!=}C\diagdown O \\ \phantom{R^1\diagdown}\overset{|}{\phantom{C}}\phantom{=\!=\!=\!=}\overset{|}{\phantom{C}} \\ A{=\!=\!=\!=}C{=\!=\!=\!=}N\diagdown B \end{array}$$

wherein either
(i) the endocyclic dotted line (-----) is a double bond; the exocyclic dotted line (-----) is a single bond;
A is $$-(O)_m-CH_2-\underset{\underset{OH}{|}}{CH}-CH_2-(O-\underset{\underset{O}{\|}}{C})_n-N\diagup^{R^3}_{\diagdown R^4};$$

m is 1; n is 0;
$R^3$ and $R^4$ are hydrogen, $C_1$-$C_4$ alkyl, benzyl or phenyl or $R^3$, $R^4$ and the nitrogen to which they are attached represent an alicyclic amino having 5 or 6 ring atoms, of which one ring atom is nitrogen and one ring atom is optionally an additional nitrogen, oxygen or sulfur heteroatom; $R^1$ is hydrogen, halogen $C_1$-$C_4$ alkyl $C_2$-$C_4$ alkenyl, $C_2$-$C_4$ alkynyl, benzyl or phenyl; and $R^2$ is hy- (Abstract continued on next page.)

drogen, $C_1$–$C_4$ alkyl phenyl or a 5- or 6- membered heterocyclic; or (ii) the endocyclic dotted line (─────) is a single bond; the exocyclic dotted line (─ ─ ─ ─) is a double bond;

A is oxygen;

B is

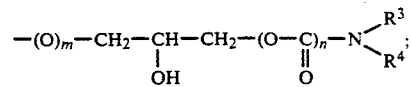

m is 0; n is 1;

$R^3$, $R^4$ and the nitrogen to which they are attached together represent an alicyclic amino group having 5 or 6 ring atoms, of which one ring atom is nitrogen and one ring atom is optionally an additional nitrogen, oxygen or sulfur heteroatom; and $R^1$ and $R^2$, together with the carbon to which they are attached, represent phenyl fused to the isoxazole ring.

2 Claims, No Drawings

USE OF ISOXAZOLIN-3-ONE DERIVATIVES AS ANTIDEPRESSANTS

This is a division of application Ser. No. 07/537,517 filed Jun. 13, 1990, now U.S. Pat. No. 5,116,839.

BACKGROUND OF THE INVENTION

The present invention relates to isoxazolin-3-one derivatives of use as antidepressants.

Senile diseases are rapidly increasing with increase int he age of the population. One such disease is senile depression. Indeed, the increase in suicide by the aged has become a social problem. Therefore, the need has arisen to develop therapeutic agents for treating such diseases.

Typical available antidepressants include imipramine (10,11-dihydro-N,N-dimethyl-5H-dibenz[b,f]azepine-5-propanamine), and mianserin hydrochloride (1,2,3,4,10,14b-hexahydro-2-methyldibenzo[c,f-]pyrazino[1,2-a]azepine hydrochloride). The need remains to develop further antidepressant compounds.

SUMMARY OF THE INVENTION

The present invention provides a method of treating depression in a patient, which method comprises administering an effective amount of a compound having the formula (I):

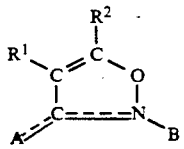

(I)

wherein:
either (a)
the endocyclic dotted line (=====) is a single bond; the exocyclic dotted line (-----) is a double bond;
A is oxygen;
B is a group of the formula (II)

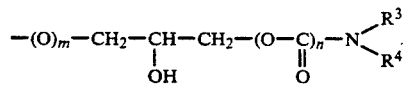

(II)

(wherein
m is 0 and n is 0 or 1;
$R^3$, $R^4$ and the nitrogen atom to which they are attached together represent an alicyclic amino group having a total of 5 or 6 ring atoms, of which one ring atom is said nitrogen atom and one ring atom is optionally an additional heteroatom selected from nitrogen, oxygen or sulfur, said alicyclic amino group being unsubstituted or, where there is an additional nitrogen heteroatom, said alicyclic amino group having a substituent of a $C_1$-$C_3$ alkyl group on said additional nitrogen heteroatom);
$R^1$ is a hydrogen atom or a halogen atom; and
$R^2$ is a phenyl group, a substituted phenyl group having as substituent at least one substituent (a) selected from the following definition for substituent (a):

substituent (a): $C_{1-3}$ alkyl groups, $C_{1-3}$ alkoxy groups, halogen atoms, or a nitro group,
a 5- or 6- membered heterocyclic group having one or more oxygen, sulfur or nitrogen atom as heteroatoms, or a substituted 5- or 6- membered heterocyclic group having one or more oxygen, sulfur or nitrogen atom as heteroatoms and having at least one substituent (a);

or (b)
the endocyclic dotted line (-----) is a double bond;
the exocyclic dotted line (-----) is a single bond;
A is a group of the formula (II)

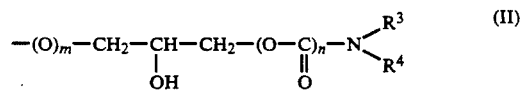

(II)

(wherein
m is 1 and n is 0;
$R^3$ and $R^4$ are be the same or different and each represents a hydrogen atom, a $C_1$-$C_4$ alkyl group, a benzyl group, a substituted benzyl group having at least One substituent (b) falling within the following definition for substituent (b):
substituent (b); $C_1$-$C_3$ alkyl groups, a $C_1$-$C_3$ alkoxy groups, a hydroxy group, halogen atoms, a nitro group, an amino group or $C_2$-$C_4$ aliphatic carboxylic acylamino groups;
a phenyl group, or a substituted phenyl group having one substituent (b); or
$R^3$, $R^4$ and the nitrogen atom to which they are attached together represent an alicyclic amino group having a total of 5 or 6 ring atoms, of which one ring atom is said nitrogen atom and one ring atom is optionally an additional heteroatom selected from nitrogen, oxygen or sulfur, said alicyclic amino group being unsubstituted or, where there is an additional nitrogen heteroatom, said alicyclic amino group having a substituent of $C_1$-$C_3$ alkyl group on said additional nitrogen heteroatom);
$R^1$ is a hydrogen atom, a halogen atom, a $C_1$-$C_4$ alkyl group, a $C_2$-$C_4$ alkenyl group, a $C_2$-$C_4$ alkynyl group, a benzyl group, a substituted benzyl group having at least one substituent (b), a phenyl group or a substituted phenyl group having at least one substituent (b);
and $R^2$ is a hydrogen atom, a $C_1$-$C_4$ alkyl group, a phenyl group, a substituted phenyl group having at least one substituent (b), a 5- or 6- membered heterocyclic group having oxygen, sulfur or nitrogen atom as heteroatoms, or a substituted 5- or 6- membered heterocyclic group having oxygen, sulfur or nitrogen atom as heteroatoms having at least one substituent (b);

or (c)
the endocyclic dotted line (=====) is a single bond;
the exocyclic dotted line (-----) is a double bond;
A is oxygen;
B is a group of the formula (II)

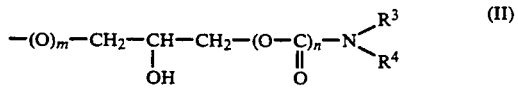

(wherein
m is 0 and n is 1;

$R^3$, $R^4$ and the nitrogen atom to which they are attached together represent an alicyclic amino group having a total of 5 or 6 ring atoms, of which one ring atom is said nitrogen atom and one ring atom is optionally an additional heteroatom selected from nitrogen, oxygen or sulfur, said alicyclic amino group being unsubstituted or, where there is an additional nitrogen heteroatom, said alicyclic amino group having a substituent of $C_1$-$C_3$ alkyl group on said additional nitrogen heteroatom);

$R^1$ and $R^2$, together with the carbon atoms to which they are attached, represent a phenyl ring fused to the isoxazole ring or a substituted phenyl ring fused to the isoxazole ring, said substituted phenyl ring having as substituent at least one substituent selected from substituents (b);

or a pharmacologically acceptable acid addition salt thereof.

It has already been reported that compounds within the general formula (I) are centrally-acting muscle relaxants (European Patent Specifications 273744 and 334674, published respectively on 06 Jul. 1988 and 27 Sep. 1989) and that they can improve brain function (European Patent Specification 334674, mentioned above, and European Patent Specification 335723 published on 04 Oct. 1990).

PREFERRED EMBODIMENTS OF THE INVENTION

Within the different definitions (a), (b) and (c), $R^1$ is a hydrogen atom; a halogen atom, such as a fluorine, chlorine or bromine atom; a $C_1$-$C_4$ alkyl group, such as a methyl, ethyl, n-propyl, isopropyl n-butyl, isobutyl, or tert-butyl group; a $C_2$-$C_4$ alkenyl group, such as a vinyl, allyl, 2-butenyl or 2-methylallyl group; a $C_2$-$C_4$ alkynyl group, such as an ethynyl or 2-propynyl group; a benzyl group; a substituted benzyl group having at least one substituent (b), which is one or more of an alkyl group containing to 3 carbon atoms such as a methyl, ethyl, n-propyl or isopropyl group, an alkoxy group containing 1 to 3 carbon atoms such as a methoxy, ethoxy, n-propoxy or isopropoxy group; a halogen atom such as fluorine, chlorine or bromine; a nitro group, an amino group or an aliphatic acylamino group typically having 2 to 4 carbon atoms, such as an acetylamino or propionylamino group; a phenyl group or a substituted phenyl group having at least one substituent (b);

$R^2$ is a hydrogen atom, a $C_1$-$C_4$ alkyl group, such as a methyl, ethyl, n-propyl, isopropyl,n-butyl, isobutyl, or tert-butyl group; a phenyl group, a substituted Phenyl group having as substituent at least one substituent (a), which is one or more of an alkyl group containing 1 to 3 carbon atoms such as a methyl, ethyl, n-propyl or isopropyl group, an alkoxy group containing 1 to 3 carbon atoms such as a methoxy, ethoxy, n-propoxy or isopropoxy group, a halogen atom such as a fluorine, chlorine or bromine atom, or a nitro group, or the Phenyl group having as substituent at least one substituent (b), as the case may be; a 5- or 6- membered heterocyclic group having one or more oxygen, sulfur or nitrogen atom as heteroatoms, such as a furyl, thienyl, thiazolyl or pyridyl group; or a substituted 5- or 6- membered heterocyclic group having one or more oxygen, sulfur or nitrogen atom as heteroatoms and having at least one substituent (a) or substituent (b), as the case may be;

or, $R^1$ and $R^2$ together with the carbon atoms to which they are attached, represent a Phenyl ring fused to the isoxazole ring or a substituted Phenyl ring fused to the isoxazole ring, said substituted Phenyl ring having as substituent at least one substituent selected from the substituents (b);

$R^3$, $R^4$ and the nitrogen atom to which they are attached together represent an alicyclic amino group having a total of 5 or 6 ring atoms, of which one ring atom is said nitrogen atom and one ring atom is optionally an additional heteroatom selected from nitrogen, oxygen or sulfur, said alicyclic amino group being unsubstituted or, where there is an additional nitrogen heteroatom, said alicyclic amino group having a substituent of a $C_1$-$C_3$ alkyl group on said additional nitrogen heteroatom, and being illustrated by a morpholino, 1-piperazinyl, 4-methyl-1-piperazinyl, 1-pyrrolidinyl or piperidino group;

or $R^3$ and $R^4$ are the same or different and each represents a hydrogen atom; a $C_1$-$C_4$ alkyl group, such as those illustrated above; a benzyl group, a substituted benzyl group having at least one substituent (b); a phenyl group; or a substituted phenyl group having one substituent (b).

In a preferred aspect, the present invention involves administering an effective amount of a compound having the formula (Ia);

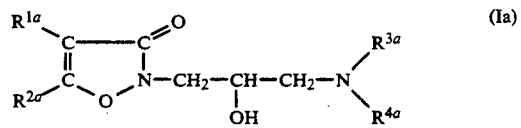

wherein:

$R^{1a}$ is a hydrogen atom or a halogen atom;

$R^{2a}$ is a phenyl group, a substituted phenyl group having as substituent at least one substituent (a), a 5- or 6- membered heterocyclic group having one or more oxygen, sulfur or nitrogen atom as heteroatoms, or a substituted 5- or 6- membered heterocyclic group having one or more oxygen, sulfur or nitrogen atom as heteroatoms and having at least one substituent (a); and $R^{3a}$, $R^{4a}$ and the nitrogen atom to which they are attached together represent an alicyclic amino group having a total of 5 or 6 ring atoms, of which one ring atom is said nitrogen atom and one ring atom is optionally an additional heteroatom selected from nitrogen, oxygen or sulfur, said alicyclic amino group being unsubstituted or, where there is an additional nitrogen heteroatom, said alicyclic amino group having a substituent of a $C_1$-$C_3$ alkyl group on said additional nitrogen heteroatom);

or a pharmacologically acceptable acid addition salt thereof.

In a further aspect, the present invention involves administering a compound of the formula (Ib):

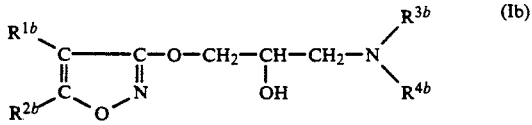

wherein:
- $R^{1b}$ is a hydrogen atom, a halogen atom, a $C_1$-$C_4$ alkyl group, a $C_2$-$C_4$ alkenyl group, a $C_2$-$C_4$ alkynyl group, a benzyl group, a substituted benzyl group having at least one substituent (b) falling within the following definition for substituent (b): substituent (b): a $C_1$-$C_3$ alkyl group, a $C_1$-$C_3$ alkoxy group, a hydroxy group, a halogen atom, a nitro group, an amino group or a $C_2$-$C_4$ aliphatic carboxylic acylamino group; a phenyl group or a substituted phenyl group having at least one substituent (b);
- $R^{2b}$ is a hydrogen atom, a $C_1$-$C_4$ alkyl group, a phenyl group, a substituted phenyl group having at least one substituent (b), a 5- or 6- membered heterocyclic group having oxygen, sulfur or nitrogen atom as heteroatoms, or a substituted 5- or 6- membered heterocyclic group having oxygen, sulfur or nitrogen atom as heteroatoms having at least one substituent (b); and
- $R^{3b}$ and are be the same or different and each represents a hydrogen atom, a $C_1$-$C_4$ alkyl group, a benzyl group, a substituted benzyl group having at least one substituent (b), a phenyl group, or a substituted phenyl group having at least one substituent (b); or
- $R^{3b}$, $R^{4b}$ and the nitrogen atom to which they are attached together represent an alicyclic amino group having a total of 5 or 6 ring atoms, of which one ring atom is said nitrogen atom and one ring atom is optionally an additional heteroatom selected from nitrogen, oxygen or sulfur, said alicyclic amino group being unsubstituted or, where there is an additional nitrogen heteroatom, said alicyclic amino group having a substituent of $C_1$-$C_3$ alkyl group on said additional nitrogen heteroatom);

or a pharmacologically acceptable acid addition salt thereof.

In a yet further aspect, the present invention involves administering a compound of the formula (Ic):

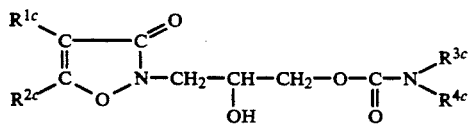

wherein
- $R^{1c}$ and $R^{2c}$, together with the carbon atoms to which they are attached, represent a phenyl ring fused to the isoxazole ring or a substituted phenyl ring fused to the isoxazole ring, said subsituted phenyl ring having as substituent at least one substituent selected from substituents (b); and
- $R^{3c}$, $R^{4c}$ and the nitrogen atom to which they are attached together represent an alicyclic amino group having a total of 5 or 6 ring atoms, of which one ring atom is said nitrogen atom and one ring atom is optionally an additional heteroatom selected from nitrogen, oxygen or sulfur, said alicyclic amino group being unsubstituted or, where there is an additional nitrogen heteroatom, said alicyclic amino group having a substituent of $C_1$-$C_3$ alkyl group on said additional nitrogen heteroatom;

or a pharmacologically acceptable acid addition salt thereof.

In the compounds of formula (Ia), $R^{1a}$ represents a hydrogen atom or a halogen atom such as a fluorine, chlorine or bromine atom.

$R^{2a}$ can represent a phenyl group, which is unsubstituted or may optionally be substituted with at least one substituent, preferably one or two substituents, where the substituents are chosen from substituents (a). The substituents (a) comprise an alkyl group containing 1 to 3 carbon atoms such as a methyl, ethyl, n-propyl or isopropyl group, an alkoxy group containing 1 to 3 carbon atoms such as a methoxy, ethoxy, n-propoxy or isopropoxy group, a halogen atom such as a fluorine, chlorine or bromine atom, or a nitro group. Particularly preferred substituents comprise one or two halogen atoms, especially one or two chlorine atoms. $R^{2a}$ can represent a 5- or 6- membered heterocyclic group having one or more oxygen, sulfur or nitrogen atom as heteroatoms, preferably one heteroatom, or such a 5- or 6- membered heterocyclic group having at least one substituent (a), preferably one or two such substituents. Examples of the heterocyclic group include a furyl, thienyl, thiazolyl or pyridyl group, and examples of the substituent (a) are given above in relation to $R^{1a}$.

$R^{3a}$ and $R^{4a}$ and the associated nitrogen atom represent a 5- or 6-membered alicyclic amino group such as a morpholino, 1-piperazinyl, 4-methyl-1-piperazinyl, 1-pyrrolidinyl or piperidino group.

In the compounds of formula (Ib), $R^{1b}$ can represent a hydrogen atom; a halogen atom such as a fluorine, chlorine or bromine atom; a straight or branched chain alkyl group containing 1 to 4 carbon atoms such as a methyl, ethyl, n-propyl, isopropyl, n-butyl, isobutyl, or tert-butyl group; a straight or branched chain alkenyl group containing 2 to 4 carbon atoms such as a vinyl, allyl, 2-butenyl or 2-methylallyl group; an alkynyl group containing 2 to 4 carbon atoms such as an ethynyl or 2-propynyl group; a benzyl group; a substituted benzyl group substituted with a substituent (b) (being an alkyl group containing 1 to 3 carbon atoms such as a methyl, ethyl, n-propyl or isopropyl group, an alkoxy group containing 1 to 3 carbon atoms such as a methoxy, ethoxy, n-propoxy or isopropoxy group; a halogen atom such as fluorine, chlorine or bromine; a nitro group, an amino group or an aliphatic acylamino group typically having 2 to 4 carbon atoms, such as an acetylamino or propionylamino group); or a phenyl group which is unsubstituted or may optionally be substituted with the substituents (b) as mentioned for the said benzyl group.

$R^{2b}$ represents a hydrogen atom; a straight or branched chain alkyl group containing 1 to 4 carbon atoms, as illustrated for the alkyl group of $R^{1b}$; a phenyl group which is unsubstituted or may optionally be substituted with the substituents (b), as illustrated above; or an optionally substituted 5- or 6-membered heterocyclic group containing an oxygen, sulfur or nitrogen atom such as furyl, thienyl, thiazolyl or pyridyl group, the optional substituents being substituents (b) as illustrated above.

Each of $R^{3b}$ and $R^{4b}$ represents a hydrogen atom; a straight or branched chain alkyl group containing 1 to 4 carbon atoms as illustrated for the alkyl group of $R^{1b}$; a benzyl or phenyl group which is unsubstituted or may optionally be substituted with the substituents (b) as illustrated above, or $R^3$ and $R^4$ with the associated nitrogen atom may represent a 5- or 6-membered alicyclic amino group such as a morpholino, 1-piperazinyl, 4-methyl-1-piperazinyl, 1-pyrrolidinyl or piperidino group.

In the compounds of formula (Ic), $R^{1c}$ and $R^{2c}$, together with the carbon atoms to which they are attached, represent a phenyl ring fused to the isoxazole ring or a substituted phenyl ring fused to the isoxazole ring. The subsituted phenyl ring has as substituent at least one substituent selected from $C_1-C_3$ alkyl groups, $C_1-C_3$ alkoxy groups, hydroxy groups, halogen atoms, nitro groups, amino groups or $C_2-C_4$ aliphatic carboxylic acylamino groups. Such groups are illustrated above with reference to substituents (b).

$R^{3c}$, $R^{4c}$ and the nitrogen atom to which they are attached together represent an alicyclic amino group having a total of 5 or 6 ring atoms, of which one ring atom is said nitrogen atom and one ring atom is optionally an additional heteroatom selected from nitrogen, oxygen or sulfur. The alicyclic amino group is unsubstituted or, where there is an additional nitrogen heteroatom, it can have a $C_1-C_3$ alkyl group on the additional nitrogen heteroatom. Suitable examples comprise a morpholino, 1-piperazinyl, 4-methyl-1-piperazinyl, 1-pyrrolidinyl or piperidino group.

Particularly preferred compounds are of formula (Ia), wherein $R^{1a}$ is a hydrogen atom or a halogen atom, especially a hydrogen atom; $R^{2a}$ is a phenyl group or a substituted phenyl group having as substituent one or two substituents, more especially one or two halogen atoms, for example a substituted phenyl group having as substituent one or two chlorine atoms; $R^{3a}$, $R^{4a}$ and the nitrogen atom to which they are attached together represent a morpholino group; and pharmacologically acceptable acid addition salts thereof, especially the hydrochloride addition salts thereof.

Pharmacologically acceptable acid addition salts of the isoxazolin-3-one derivatives of the said general formula (I) include, for example, salts of a mineral acid such as a hydrochloride, hydrobromide or sulfate salt, or salts of an organic acid such as an oxalate, lactate, citrate, tartarate, succinate, maleate, fumarate or methanesulfonate salt.

The compounds of the said general formula (I) exist as optical isomers, owing to the presence of at least one asymmetric carbon atom. The present invention extends to such isomers and mixtures thereof, including racemic mixtures.

Examples of preferred compounds of the general formula (1) include the following list of compounds which are numbered in sequence for further reference, and pharmaceutically acceptable salts of these compounds, especially the hydrochlorides of these compounds. In the list, for compounds of formula (Ia) where $R^{3a}$ and $R^{4b}$ form an alicyclic amino group with the nitrogen to which they are attached, there is a single entry under $R^{3a}$ and $R^{4a}$. Similar considerations apply to the substituents of compounds of the other formulae.

In the list, the following abbreviations are employed:

| | |
|---|---|
| Phe | phenyl |
| Pyrd | pyrrolidinyl |
| Mor | morpholino |
| Piz | piperazinyl |
| Me | methyl |
| Pip | piperidyl |
| Nox | nitro |
| MeO | methoxy |
| Thi | thienyl |
| Et | ethyl |
| Pr | propyl |
| iPr | isopropyl |
| Bu | butyl |
| iBu | isobutyl |
| sBu | sec-butyl |
| tBu | tert-butyl |
| Hex | hexyl |
| Bz | benzyl |
| All | allyl |
| Buen | butenyl |
| Pryn | propynyl |

Compounds of formula (Ia):

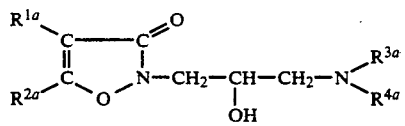

| No. | $R^{1a}$ | $R^{2a}$ | $R^{3a}$ | $R^{4a}$ |
|---|---|---|---|---|
| 1 | H | Phe | 1-Pyrd | |
| 2 | H | Phe | Mor | |
| 3 | H | Phe | 1-Piz | |
| 4 | H | Phe | 4-Me-1-Piz | |
| 5 | H | Phe | 1-Pip | |
| 6 | Cl | Phe | 1-Pyrd | |
| 7 | Cl | Phe | Mor | |
| 8 | Cl | Phe | 1-Piz | |
| 9 | Cl | Phe | 4-Me-1-Piz | |
| 10 | Cl | Phe | 1-Pip | |
| 11 | H | 4-ClPhe | Mor | |
| 12 | H | 3-ClPhe | Mor | |
| 13 | H | 4-NoxPhe | Mor | |
| 14 | H | 4-MeOPhe | Mor | |
| 15 | H | 3-MeOPhe | Mor | |
| 16 | H | 2-MeOPhe | Mor | |
| 17 | H | 4-OHPhe | Mor | |
| 18 | H | 4-FlPhe | Mor | |
| 19 | H | 2,4-diClPhe | Mor | |
| 20 | H | 2-Thi | Mor | |
| 21 | H | 3-Pyr | Mor | |
| 22 | H | (S)-4-ClPhe | Mor | |

Compounds of formula (Ib):

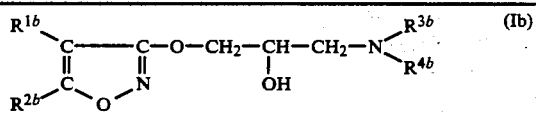

| No. | $R^{1b}$ | $R^{2b}$ | $R^{3b}$ | $R^{4b}$ |
|---|---|---|---|---|
| 23 | H | Phe | H | H |
| 24 | H | Phe | H | Me |
| 25 | H | Phe | H | Et |
| 26 | H | Phe | H | Pr |
| 27 | H | Phe | H | iPr |
| 28 | H | Phe | H | Bu |
| 29 | H | Phe | H | iBu |
| 30 | H | Phe | H | sBu |
| 31 | H | Phe | H | Hex |
| 32 | H | Phe | H | Phe |
| 33 | H | Phe | H | Bz |
| 34 | H | Phe | Me | Me |
| 35 | H | Phe | 1-Pyrd | |

-continued $$R^{1b}_{R^{2b}}C=C-O-CH_2-CH-CH_2-N\begin{array}{c}R^{3b}\\R^{4b}\end{array} \quad (Ib)$$
$$\phantom{R^{2b}C=C}\phantom{OOOOOO}OH$$

| No. | $R^{1b}$ | $R^{2b}$ | $R^{3b}$ | $R^{4b}$ |
|---|---|---|---|---|
| 36 | H | Phe | | Mor |
| 37 | H | Phe | | 1-Piz |
| 38 | H | Phe | | 4-Me-1-Piz |
| 39 | H | Phe | | 1-Pip |
| 40 | Cl | Phe | H | H |
| 41 | Cl | Phe | H | Me |
| 42 | Cl | Phe | H | Et |
| 43 | Cl | Phe | H | Pr |
| 44 | Cl | Phe | H | iPr |
| 45 | Cl | Phe | H | Bu |
| 46 | Cl | Phe | H | iBu |
| 47 | Cl | Phe | H | sBu |
| 48 | Cl | Phe | H | tBu |
| 49 | Cl | Phe | H | Phe |
| 50 | Cl | Phe | H | Bz |
| 51 | Cl | Phe | Me | Me |
| 52 | Cl | Phe | | 1-Pyrd |
| 53 | Cl | Phe | | Mor |
| 54 | Cl | Phe | | 1-Piz |
| 55 | Cl | Phe | | 4-Me-1-Piz |
| 56 | Cl | Phe | | 1-Pip |
| 57 | Me | Phe | H | H |
| 58 | Me | Phe | | Mor |
| 59 | iPr | Phe | | Mor |
| 60 | iBu | Phe | | Mor |
| 61 | All | Phe | | Mor |
| 62 | 2-Buen | Phe | | Mor |
| 63 | 2-Pryn | Phe | | Mor |
| 64 | Phe | Phe | | Mor |
| 65 | Bz | Phe | | Mor |
| 66 | H | H | | Mor |
| 67 | H | Et | H | H |
| 68 | H | Me | | Mor |
| 69 | H | Pr | | Mor |
| 70 | H | iPr | | Mor |
| 71 | H | Bu | | Mor |
| 72 | H | iBu | | Mor |
| 73 | H | sBu | | Mor |
| 74 | H | tBu | | Mor |
| 75 | Cl | Me | | Mor |
| 76 | H | 4-ClPhe | | Mor |
| 77 | H | 3-ClPhe | | Mor |
| 78 | H | 4-NoxPhe | | Mor |
| 79 | H | 4-MeOPhe | | Mor |
| 80 | H | 3-MeOPhe | | Mor |
| 81 | H | 2-MeOPhe | | Mor |
| 82 | H | 4-OHPhe | | Mor |
| 83 | H | 4-FlPhe | | Mor |
| 84 | H | 2,4-diClPhe | | Mor |
| 85 | H | 2-Thi | | Mor |
| 86 | H | 3-Pyr | | Mor |

Compounds of formula (Id):

$$R^5\phantom{xxxxxxxxxxxxxxxxxxxxxxxx}(Id)$$
$$R^6\!-\!\!\bigcirc\!\!\!\overset{O}{\underset{O-N-CH_2-CH-CH_2-O-C-N}{\|}}R^{3d}_{R^{4d}}$$
$$\phantom{xxxxxxxxxxxxxxxxxxxxx}OH\phantom{xx}O$$

| No. | $R^{3d}$ | $R^{4d}$ | $R^5$ | $R^6$ | $R^7$ | $R^8$ |
|---|---|---|---|---|---|---|
| 86 | H | H | H | H | H | H |
| 87 | H | H | H | Cl | H | H |
| 88 | H | Et | H | H | H | H |
| 89 | H | Pr | H | H | H | H |
| 90 | H | iPr | H | H | H | H |
| 91 | H | Bu | H | H | H | H |
| 92 | H | iBu | H | H | H | H |
| 93 | H | sBu | H | H | H | H |

-continued $$R^5\phantom{xxxxxxxxxxxxxxxxxxxxxxxx}(Id)$$
$$R^6\!-\!\!\bigcirc\!\!\!\overset{O}{\underset{O-N-CH_2-CH-CH_2-O-C-N}{\|}}R^{3d}_{R^{4d}}$$
$$\phantom{xxxxxxxxxxxxxxxxxxxxx}OH\phantom{xx}O$$

| No. | $R^{3d}$ | $R^{4d}$ | $R^5$ | $R^6$ | $R^7$ | $R^8$ |
|---|---|---|---|---|---|---|
| 94 | H | tBu | H | H | H | H |
| 95 | H | Phe | H | H | H | H |
| 96 | H | Bz | H | H | H | H |
| 98 | Me | Me | H | H | H | H |
| 99 | 1-Pyrd | | H | H | H | H |
| 100 | Mor | | H | H | H | H |
| 101 | 1-Piz | | H | H | H | H |
| 102 | 4-Me-1-Piz | | H | H | H | H |
| 103 | 1-Pip | | H | H | H | H |
| 104 | H | Me | H | H | H | Cl |
| 105 | H | Et | H | H | H | Cl |
| 106 | H | Pr | H | H | H | Cl |
| 107 | H | iPr | H | H | H | Cl |
| 108 | H | Bu | H | H | H | Cl |
| 109 | H | iBu | H | H | H | Cl |
| 110 | H | sBu | H | H | H | Cl |
| 111 | H | tBu | H | H | H | Cl |
| 112 | H | Phe | H | H | H | Cl |
| 113 | H | Bz | H | Cl | H | H |
| 114 | H | Me | H | Cl | H | H |
| 115 | 1-Pyrd | | H | Cl | H | H |
| 116 | Mor | | H | Cl | H | H |
| 117 | 1-Piz | | H | Cl | H | H |
| 118 | 4-Me-1-Piz | | H | Cl | H | H |
| 119 | 1-Pip | | H | Cl | H | H |
| 120 | H | H | H | Cl | H | H |
| 121 | H | H | H | H | H | Me |
| 122 | H | H | H | $NH_2$ | H | H |
| 123 | H | H | H | $NHCOCH_3$ | H | H |
| 124 | H | H | H | OMe | H | H |

Compounds 2, 11, 12, 18, 19 and 22, their hydrochlorides are preferred, with Compounds 11 and 22 and their hydrochlorides being most preferred.

It has been shown by pharmacological tests that the compounds of the said general formula (I) according to the present invention exhibit anti-reserpine activity and the potentiation of spontaneous locomotion upon administration of monoamine precursors such as L-DOPA and L-5-HTP. The procedure employed in the tests will be explained concretely below Effect on reserpine-induced ptosis in the mouse Male ddY mice (4 weeks of age, body weight 22–27 g) were used, divided into the indicated groups each consisting of 3 or 6 animals. The test compounds were dissolved or suspended in an appropriate solvent (physiological saline, 0.5% CMC or 1% dimethylsulfoxide solution) and were orally administered immediately before treatment with reserpine. The animals of the control groups were given corresponding vehicles in a similar manner. A reference compound, imipramine.hydrochloride, was also dissolved in physiological saline and administered in a similar manner.

The vials containing the test solutions were labeled with coded ciphers and the administration was carried out in randomized order. The scorer therefore did not know which samples had been given to which mice.

The mice were then subcutaneously treated with reserpine at a dose of 2 mg/kg. After 90 minutes, the extent of ptosis was scored. Grading of the score was based on the shape of eye immediately after the mice were taken out from their cages;

| | |
|---|---|
| 0 | round eye shape, as normal |
| 1 | ⅓ eyelid closing |
| 2 | ⅔ eyelid closing |
| 3 | closed eyelid. |

The inhibition rate at each dose was calculated from the scores according to the following equation:

Inhibition rate (%) =

$$\left(1 - \frac{\text{sum of scores in a group given test compound}}{\text{sum of scores in control group given vehicle}}\right) \times 100$$

The inhibition rate was then scored on the following basis:

| inhibition rate | score |
|---|---|
| 71% or more | + |
| 41% to 70% | ± |
| 40% or less | − |

Results on antagonism against reserpine-induced ptosis in mice

| Compound | Dosage (mg/kg) | Number of mice | Inhibition rate (%) | Score |
|---|---|---|---|---|
| Compound 11 | 3 | 6 | 50 | ± |
| Compound 11 | 10 | 6 | 56 | ± |
| Compound 11 | 30 | 6 | 72 | + |
| Compound 22 | 3 | 6 | 56 | ± |
| Compound 22 | 10 | 6 | 81 | ± |
| Compound 22 | 30 | 6 | 100 | + |
| Compound 36 | 100 | 3 | 71 | + |
| Compound 53 | 30 | 3 | 55 | ± |
| Compound 76 | 100 | 3 | 71 | + |
| Compound 87 | 30 | 3 | 75 | + |
| Compound 87 | 100 | 3 | 100 | + |
| Imipramine.HCl | 30 | 6 | 61 | ± |

2. Potentiating effect of compounds upon spontaneous locomotor activities in mice treated with L-DOPA Male ddY mice (5 weeks old, body weight 30-33 g) were used, after divided into groups each consisting of 5 animals (experiment 1) or 15 animals (experiment 2). The test compounds were prepared as described in the anti-reserpine study, and given orally 20 minutes before administration of MK-486. In control animals, saline was similarly administered. In order to Prevent decomposition of L-DOPA at the peripheral site, the mice were intraperitoneally given MK-486 (carbidopa) at a dose of 20 mg/kg and treated intraperitoneally 30 minutes later with L-DOPA. The mice were Placed in a cage on a locomotor activity counter (AUTOMEX-11), one-by-one (experiment 1) or 3 mice a cage (experiment 2). Spontaneous locomotor activities were determined for an hour and the average locomotor activity at each dose was calcultated from 5 counts. The spontaneous locomotor activity in animals treated with the compound was statistically analyzed versus the control group using Student's two-tailed t-test.

Results of potentiating effects of compounds upon spontaneous locomotor activities in mice given L-DOPA

| Compound | Dose (mg/kg) | Number of mice | Average locomotor activities (+/−S.E.) | P |
|---|---|---|---|---|
| Control | — | 5 | 160(+/−128) | |
| Compound 11 | 50 | 5 | 3355(+/−878) | <0.05 |
| Control | — | 15 | 666(+/−137) | |
| Compound 22 | 50 | 15 | 6013(+/−629) | <0.001 |

As shown, Compound 11, and particularly its (S) isomer which is Compound 22, significantly increased the spontaneous locomotor activity with treatment of L-DOPA at a dose of 50 mg/kg.

3. Potentiating effect of compounds upon spontaneous locomotor activities in mice treated with L-5-HTP Male ddY mice (4 weeks old, body weight 22-25 g) were used, after divided into groups each consisting of 15 mice. Before administration of MK-486 (20 mg/kg, IP), either the test compound formulation or vehicle (control group) was orally administered. At 30 min after administration of MK-485, L-5-HTP (100 mg/kg IP) was injected. Spontaneous locomotor activities were determined from 15 minutes after L-5-HTP. For this determination, 3 mice were placed in a locomotor counter (Automex) for an hour and the total count noted. Five such apparatuses were used for each dose, in order to eliminate different sensitivities of each apparatus. Thus, 15 mice were used in total for each dose. The average count and SE were calculated from the 5 determinations for each dose, and statistically analyzed versus control group using Student's two-tailed t-test.

Results of potentiating effects of compounds upon spontaneous locomotor activities in mice given L-OOPA

| Compound | Dose (mg/kg) | Average spontaneous locomotor activity | P |
|---|---|---|---|
| saline | — | 2147(+/−334) | |
| Compound 22 | 3 | 3544(+/−318) | <0.01 |

As shown, Compound 22, which is the (S) isomer of Compound 11, significantly potentiated (P<0.01) the spontaneous locomotor activity on treatment with L-5-HTP at a dose of 3 mg/kg.

4. Acute toxicity

Each of the Compounds 11, 36 (as its hydrochloride), 53, 76, and 87 dissolved in a 0.5% CMC solution was orally administered to 5 mice at a dose of 300 mg/kg. Observations were made for a period of 5 days. No particular symptoms were detected and all the mice survived.

From these results, it can be seen that the compounds of the general formula (I) show low toxicity without inducing drowsiness, and exhibit an antidepressant activity, such as an anti-reserpine activity and a L-DOPA promoting activity. Furthermore, there is evidence to suggest that the present compounds do not show the anticholinergic activity which is apparently exerted by imipramine, and have a considerably different mode Of action to mianserin.

The compounds can be administered clinically by the parental route or by the oral route. They exhibit good absorbability by the oral route, especially since the hydrochloride or other salt is soluble in water. By way of example, the oral route include the form of tablets, capsules, granules, powders, syrups or the like, and suitable formulations for the parenteral route include injections, suppositories or the like.

The pharmaceutical preparations of this invention can be produced according to the conventional manner using the adjuvants generally known in the art of the field, such as one or more of an excipient, binder, disintegrator, lubricant, corrective or the like. The dosage may vary depending upon the symptom, age, body weight and other factors relating to the Patient, but in case of oral administration to adults, the active compound is usually administered at a dose of from 3 mg to 100 mg (especially 10–50 mg) once to three times a day.

Isoxazolin-3-one derivatives of the general formula (1), and salts thereof, can be prepared by methods already reported in the literature. For example, the compounds can be prepared by adoption of methods and starting materials described in European Patent Specification 273744, European Patent Specification 334674. European Patent Specification 335723, Japanese patent Provisional Publication No. Sho 56-34674, Japanese Patent Provisional Publication No. Sho 52-31070, and Japanese patent provisional Publication No. Sho 55-83766 among others, the disclosure of which is incorporated by reference.

EXAMPLES OF THE INVENTION

The following Examples illustrate the preparation of typical compounds of the invention from known starting compounds or from starting compounds which may be prepared using Procedures analogous to those employed for known compounds. Formulation Examples are also given. A Reference Example is also included for the preparation of a starting compounds.

EXAMPLE 1

(S)-5-(p-Chlorophenyl)-2-(2-hydroxy-3-morpholinopropyl)isoxazolin-3-one.hydrochloride 1-(a):
(R)-2-(3-Chloro-2-hydroxypropyl)-5-(p-chlorophenyl)-isoxazolin-3-one 5-(p-Chlorophenyl)-3-hydroxyisoxazole (80.0 g) was slowly added at 80° C. to a toluene solution (80 ml) of (R)-(−)epichlorohydrin (50.0 g), and the reaction solution was stirred for 20 hours at 80°–85° C. After cooling the reaction solution, the deposited crystalline precipitate was washed with cold toluene (200 ml) to give 85.8 g of the desired product.

Yield 72.8%, melting point 135+ to 136+ C.
Elemental Analysis, $C_{12}H_{11}NO_3Cl_2$:
calcd: C, 50.02; H, 3.85; N, 4.86; Cl, 24.61.
found: C, 50.09; H, 3.98; N, 4.89; Cl, 24.55.
IR spectra $\gamma$max (KBr) cm$^{-1}$:
3231, 1642, 1628.
NMR spectra (CDCl$_3$) $\delta$ ppm:
3.56–3.76 (2H, multiplet),
4.10–4.40 (3H, multiplet),
6.05 (1H, singlet),
7.48 (2H, doublet, J =9.0 Hz),
7.60 (2H, doublet, J =9.0 Hz).

1-(b):
(S)-5-(p-Chlorophenyl)-2-(2-hydroxy-3-morpholinopropyl)isoxazolin-3-one

In an ethanol solution (800 ml) of 80.0 g of the product of step 1-(a), morpholine (29.0 g) and potassium carbonate (46.0 g) were refluxed for 6 hours After cooling, the reaction solution was concentrated under reduced pressure, and the resulting residue was dissolved in ethyl acetate (800 ml), then washed with 10% sodium chloride solution, and dried over anhydrous magnesium sulfate. After concentration of the reaction solution under reduced pressure, the resulting solid was recrystallized with ethyl acetate to give 84.3 g of the desired product.

Yield 89.8%, melting point 121° to 123° C.,
Elemental Analysis, $C_{16}H_{19}N_2O_4Cl$:
calcd: C, 56.72; H, 5.65; N, 8.27; Cl, 10.46.
found: C, 56.69; H, 5.77; N, 8.14; Cl, 10.19.
IR spectra $\lambda$max (KBr) cm$^{-1}$:
3326, 1655, 1636.
NMR spectra (CDCl$_3$) $\delta$ ppm:
2.40–2.75 (2H ×3, multiplet),
3.72 (2H ×2, triplet, J =6.0 Hz),
6.02 (1H, singlet),
7.46 (2H, doublet, J =9.0 Hz),
7.60 (2H, doublet, J =9.0 Hz).

1-(c):
(S)-5-(p-Chlorophenyl)-2-(2-hydroxy-3-morpholinopropyl)isoxazolin-3-one hydrochloride 4N-HCl/dioxane (50 ml) was slowly dropped in an ethanol solution (600 ml) of 60.0 g of the product of step 1-(b) at 5° C., and the reaction solution was stirred for 5 minutes. After concentration of the reaction solution under reduced pressure, the resulting solid was recrystallized with ethanol to give 61.5 g of the desired product.

Yield 92.5%, melting point 210°–213° C. (decompd.),
Elemental Analysis, $C_{16}H_{20}N_2O_4Cl_2$:
calcd: C, 51.21; H, 5.37; N, 7.47; Cl, 18.90.
found: C, 51.15; H, 5.27; N, 7.59; Cl, 18.66.
IR spectra $\lambda$max (KBr) cm$^{-1}$:
3266, 1671.
NMR spectra (CDCl$_3$) $\delta$ ppm:
3.05–40 (2H ×5, multiplet),
3.95 (1H, doublet, J =2. 4 Hz),
3.97 (1H, singlet),
4.33–4. 43 (1H, multiplet),
6.07 (1H, singlet),
7.33 (2H, doublet, J =9.0 Hz),
7.60 (2H, doublet, J =9.0 Hz).
$^{23}[a]_D$ −2.0° (c =1.0, H$_2$O).

EXMAPLE 2

3-(2-Hydroxy-3-morpholinopropoxy)-5-phenylisoxazole.hydrochloride 2-(a):
3-(2-Hydroxy-3-morpholinopropoxy)-5-phenylisoxazole To a solution of 40.0 g of 3-(2,3-epoxypropoxy)-5-phenylisoxazole dissolved in ethanol (400 ml) was added 17.6 g of morpholine and the mixture was refluxed by heating for 5 hours, followed by concentration under reduced pressure. The resulting solid was recrystallized from ethyl acetate to afford 50.0 g of the title compound with melting point 123°–124° C. as colorless columns.

IR spectrum (KBr) cm$^{-1}$:
3190, 1624, 1511, 1440.
NMR spectrum (CDCl$_3$) $\delta$ ppm:
2.30–2.85 (2H ×3, multiplet),
3.20–3.70 (1H, broad),
3.73 (2H ×2, triplet, J =4.5),
3.90–4.55 (1H, multiplet), 4.15-4.50, (2H, multiplet),
6.18 (1H, singlet),
7.35-7.85 (5H, multiplet).

2-(b):
3-(2-Hydroxy-3-morpholinopropoxy)-5-phenylisoxazole.hydrochloride

To a solution of 5.00 g of 3-(2-hydroxy-3-morpholinopropoxy-5-phenylisoxazole dissolved in ethyl acetate (200 ml) was added a 4N HCl/dioxane solution (5.0 ml) and the mixture was stirred at room temperature for 10 minutes. The reaction mixture was concentrated under reduced pressure to afford 5.21 g of the title compound with melting point 149°-150° C. as colorless powdery crystals.

IR spectrum (KBr) cm$^{-1}$:
3215, 1625, 1513, 1461.
NMR spectrum (D$_2$O) δ ppm:
3.66-4.13 (2H ×3, multiplet),
4.50 (2H ×2, triplet, J =4.5),
4.69 (2H, doublet, J =4.5),
4.80-5.20 (1H, multiplet),
6.83 (1H, singlet),
7.80-8.30 (5H, multiplet).

EXAMPLES 3 to 8

Following a similar procedure to that of Example 2, the compounds of Examples 3 to 8 listed below were synthesized.

| Example | Compound | Melting Point (°C.) |
| --- | --- | --- |
| 3 | 4-Chloro-3-(2-hydroxy-3-morpholino-propoxy)-5-phenylisoxazole | 75-76 |
| 4 | 5-(p-Chlorophenyl)-3-(2-hydroxy-3-morpholinopropoxy)isoxazole | 114-115 |
| 5 | 3-(3-n-Hexylamino-2-hydroxypropoxy)-5-phenylisoxazole | 115-116 |
| 6 | 5-(m-Chlorophenyl)-3-(2-hydroxy-3-morpholinopropoxy)isoxazole | 76-77 |
| 7 | 4-Chloro-3-(2-hydroxy-3-morpholino-propoxy)-5-phenylisoxazole.HCl | 200-202 (decomp.) |
| 8 | 3-(2-Hydroxy-3-morpholinopropoxy)-4-methyl-5-phenylisoxazole | 94-95 |

EXAMPLE 9

2-(3-Carbamoyloxy-2-hydroxypropyl)-5-chlorobenzoisoxazolin-3-one

To a solution of 1.00 g of 5-chloro-2-(2,3-dihydroxypropyl)-1,2-benzoisoxazolin-3-one in tetrahydrofuran (20 ml) was added 0.40 g of trichloromethyl chloroformate and the mixture was stirred at room temperature. After 30 minutes, the reaction mixture was cooled to 5° C. followed by adding dropwise 0.42 g of triethylamine. After stirring at the same temperature for 30 minutes, 5.0 ml of a 28% ammonia solution was added. Furthermore, after stirring at room temperature for 2 hours, the reaction mixture was refluxed by heating for 3 hours followed by concentration under reduced pressure. The residue was dissolved in ethyl acetate (100 ml) and the solution was washed with a 10% NaCl solution. The organic layer was dried over anhydrous magnesium sulfate and the drying agent was removed by filtration. The solvent was distilled off under reduced pressure and the residue was purified by column chromatography (developing solvent: ethyl acetate) through silica gel to afford 0.75 g (64.1%) of the title compound having melting point 161°-162° C. as a colorless powder.

IR spectrum (KBr) cm$^{-1}$:
3420, 3320, 3260, (OH, NH$_2$), 1683, 1662 (C=O),
NMR spectrum (DMSO-d$_6$) δ ppm:
3.86-4.46 (5H, broad),
5.31 (1H, doublet, J =4.5),
6.50 (2H, singlet),
7.46-7.90 (3H, multiplet).

FORMULATION EXAMPLE 1

| Tablets | |
| --- | --- |
| 5-p-chlorophenyl-2-(2-hydroxy-3-morpholinopropyl)-4-isoxazolin-3-one | 10.0 mg |
| lactose | 83.3 mg |
| corn starch | 25.0 mg |
| HPC (Nippon Soda Co., Ltd.) | 1.2 mg |
| magnesium stearate | 0.5 mg |
| Total | 120 mg |

Adopting a conventional procedure, tablets each weighing 120 mg were made from the ingredients comprising the above formulation.

FORMULATION EXAMPLE 2

| Capsule | |
| --- | --- |
| 3-(2-hydroxy-3-morpholinopropoxy)-5-phenylisoxazole.hydrochloride | 25.0 mg |
| lactose | 153.6 mg |
| corn starch | 100.0 mg |
| magnesium stearate | 1.4 mg |
| Total | 280.0 mg |

The powders of the above prescription were mixed, passed through a 60 mesh sieve, and 280 mg portions of the resulting powder was packed into No.3 gelatin capsules.

FORMULATION EXAMPLE 3

| Capsule | |
| --- | --- |
| 2-(3-carbamoyloxy-2-hydroxypropyl)-5-chlorobenzoisoxazolin-3-one | 25.0 mg |
| lactose | 153.6 mg |
| corn starch | 100.0 mg |
| Magnesium stearate | 1.4 mg |
| Total | 280.0 mg |

The starch powder in the above prescription was mixed, Passed through a 60 mesh sieve, and 280 mg Portions of the resulting Powder was Packed into No.3 gelatin capsules.

REFERENCE EXAMPLE 1

3-(2,3-Epoxypropoxy)-5-phenylisoxazole

To a solution of 10.00 g of 3-hydroxy-5-phenylisoxazole dissolved in hexamethylphosphoroamide (50 ml) were added 10.28 g of anhydrous Potassium carbonate and 6.89 g of epichlorohydrin, and the mixture was stirred at room temperature for 24 hours. After insoluble materials in the reaction mixture were removed by filtration, the filtrate was diluted with ethyl acetate (200 ml) followed by washing with an aqueous 10% sodium chloride solution (200 ml ×2). After the organic layer was dried over anhydrous magnesium sulfate, the drying agent was filtered off and the filtrate was freed from the solvent by distillation under reduced Pressure. The residue was purified by column chromatography through silica gel (developing solvent: a 4:1 mixture of cyclohexane and ethyl acetate) to afford 11 00 g (82.0%) of the title compound with melting point 98° to 99° C. as colorless needles.

IR spectrum (KBr) cm$^{-1}$:
1615, 1585, 1511, 1459, 1418.
NMR spectrum (CDCl$_3$) δ ppm:
2.73 (1H, AB-doublet of doublets, J =4.5, 3.0),
2.87 (1H, AB-doublet of doublets, J =4.5, 4.5),
3.26-3.50 (1H, multiplet),
4.20 (1H, AB-doublet of doublets, J =12.0, 6.0),
4.58, (1H, AB-doublet of doublets, J =12.0, 3.0),
6.20 (1H, singlet),
7.30-7.90 (5H, multiplet).

We claim:

1. A method of treating depression in a patient, which method comprises administering to a patient in need thereof an effective amount of a compound having the formula I (c):

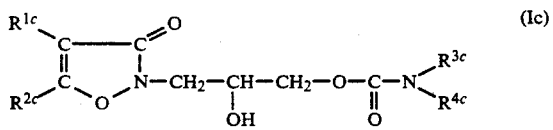

wherein:

$R^{1c}$ and $R^{2c}$, together with the carbon atoms to which they are attached, represent an unsubstituted phenyl ring fused to the isoxazole ring or a substituted phenyl ring fused to the isoxazole ring, said substituted phenyl ring having as a substituent at least one substituent selected group, a $C_1$-$C_3$ alkoxy group, a hydroxy group, a halogen atom, a nitro group, an amino group and a $C_2$-$C_4$ aliphatic carboxylic acylamino group; and $R^{3c}$, $R^{4c}$ and the nitrogen atom to which they are attached together represent an alicyclic amino group having a total of 5 or 6 ring atoms, of which one ring atom is said nitrogen atom and one ring atom is optionally an additional heteroatom selected from the group consisting of nitrogen, oxygen and sulfur, said alicyclic amino group being unsubstituted or, where there is an additional nitrogen heteroatom, said alicyclic amino group having a substituent of a $C_1$-$C_3$ alkyl group on said additional nitrogen heteroatom;

or a pharmacologically acceptable acid addition salt thereof.

2. The method according to claim 1, wherein $R^{1c}$ and $R^{2c}$ is an unsubstituted or substituted phenyl ring fused to the isoxazole ring, wherein said substituted phenyl ring is substituted by a substituent selected from the group consisting of methyl, ethyl, n-propyl, isopropyl, fluorine, chlorine, bromine, nitro, amino, acetylamino and propionylamino; and $R^{3c}$, $R^{4c}$ and the nitrogen atom which they are attached together form an alicyclic amino group selected from the group consisting of morpholino, 1-piperazinyl, 4-methyl-1-piperazinyl, 1-pyrrolidinyl and piperidino.

* * * * *